United States Patent
Eijsbouts et al.

(10) Patent No.: US 10,525,453 B2
(45) Date of Patent: Jan. 7, 2020

(54) CROSS-LINKED POLYSTYRENE CATALYST, METHOD OF MAKING, AND USES THEREOF

(71) Applicant: SABIC GLOBAL TECHNOLOGIES B.V., Bergen op Zoom (NL)

(72) Inventors: Paulus Johannes Maria Eijsbouts, Nieuwkuijk (NL); Nathalie Gonzalez Vidal, Bergen op Zoom (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/089,513

(22) PCT Filed: Jun. 22, 2017

(86) PCT No.: PCT/IB2017/053748
§ 371 (c)(1),
(2) Date: Sep. 28, 2018

(87) PCT Pub. No.: WO2017/221205
PCT Pub. Date: Dec. 28, 2017

(65) Prior Publication Data
US 2019/0105645 A1    Apr. 11, 2019

(30) Foreign Application Priority Data
Jun. 24, 2016  (EP) .................................. 16176154

(51) Int. Cl.
*C07C 37/20*    (2006.01)
*B01J 31/00*    (2006.01)
*B01J 37/00*    (2006.01)
*B01J 31/10*    (2006.01)
*B01J 37/02*    (2006.01)
*B01J 37/06*    (2006.01)

(52) U.S. Cl.
CPC ............ *B01J 31/10* (2013.01); *B01J 37/0217* (2013.01); *B01J 37/0221* (2013.01); *B01J 37/06* (2013.01); *C07C 37/20* (2013.01); *B01J 2231/347* (2013.01)

(58) Field of Classification Search
CPC ........... B01L 31/10; B01L 31/37; C07C 37/20
See application file for complete search history.

(56) References Cited

U.S. PATENT DOCUMENTS

| 4,596,858 A | 6/1986 | Gregor et al. |
| 6,730,816 B2 | 5/2004 | Lundquist |
| 7,132,575 B2 | 11/2006 | Carvill et al. |
| 8,017,724 B2 | 9/2011 | Yanagawa et al. |
| 2002/0147241 A1 | 10/2002 | Kissinger et al. |
| 2010/0273901 A1 | 10/2010 | Ehrenberg et al. |

FOREIGN PATENT DOCUMENTS

| CN | 1772774 A | 5/2006 |
| CN | 103159876 A | 6/2013 |

OTHER PUBLICATIONS

International Search Report; International Application No. PCT/IB2017/053748; International Filing Date: Jun. 22, 2017;dated Aug. 30, 2017; 5 pages.
K.W. Pepper, "Sulphonated cross-linked polystyrene: A monofunctional cation-exchange resin," 2007, vol. 1, Issue 3.
Ordomsky et al.; "Foam supported sulfonated polystyrene as a new acidic material for catalytic reactions"; Chem. Eng. J.; 2012; 8 pages.
Ozer et al. "Crosslinked PS-DVB microspheres with sulfonated polystyrene brushes as new generation of ion exchange resins," Jan. 15, 2013, Desalination, vol. 309, pp. 141-147.
Reinicker et al. "Bisphenol a synthesis: Kinetics of the phenol-acetone condensation reaction catalyzed by sulfonic acid resin," Sep. 1974, AIChE Journal; vol. 20, Issue 5, pp. 933-940.
Sakura et al. "Efficient production of bisphenol-A by utilizing cation-exchange polystyrene resins that arecrosslinked by naphthalene or a biphenyl unit," Jan. 2014, Polymer Journal 46, pp. 82-84.
Written Opinion; International Application No. PCT/IB2017/053748; International Filing Date: Jun. 22, 2017;dated Aug. 30, 2017; 6 pages.

*Primary Examiner* — Sikarl A Witherspoon
(74) *Attorney, Agent, or Firm* — Cantor Colburn LLP (57) ABSTRACT

In an embodiment, a catalyst comprises a porous carrier having 5 to 200 pores per 2.54 centimeters and a pore volume of at least 90 vol % based on the total volume of the porous carrier; wherein the porous carrier comprises one or both of carbon and a metal; and a sulfonated, cross-linked polystyrene located on at least part of a surface of the porous carrier.

18 Claims, 3 Drawing Sheets

CROSS-LINKED POLYSTYRENE CATALYST, METHOD OF MAKING, AND USES THEREOF

CROSS-REFERENCE TO RELATED APPLICATIONS

This application is a National Stage application of PCT/IB2017/053748, filed Jun. 22, 2017, which claims the benefit of European Application No. 16176154, filed Jun. 24, 2016, both of which are incorporated by reference in their entirety herein.

BACKGROUND

Over the years, many different catalysts have been developed for producing bisphenol A (BPA). For example, US 2002/0147241 discloses an ion exchange bed for producing bisphenol A from phenol and acetone in a fixed bed reactor containing a gel-form or macroporous sulfonic acid ion exchange resin catalyst bed that has an upper layer and a lower layer and EP1222960A3 discloses a catalyst for producing bisphenol A that comprises strongly acidic cation-exchange resin spheres produced from a polystyrene/divinylbenzene (PS/DVB) copolymer sulfonated under conditions to introduce sulfone cross-linking.

In general, commercial processes for producing bisphenols, for example, BPA, typically use sulfonated, cross-linked polystyrene ion exchange resins (IER) with a mercapto co-promoter. These ion exchange resins are either 2 or 4% cross-linked polystyrene with divinylbenzene as the cross-linking agent and are either mono- or polydispersed materials with a typical particle size of 300 to 1,200 micrometers. The particles are gel-like in nature, which means that the reactants need to diffuse to a great extent into the particle to get to the active sulfonic acid sites and the resultant products then need to diffuse out. Due to the slow diffusion in the gel-like matrix of the ion exchange resin particles, the resulting commercial reactors are big vessels, have long residence times for the reaction, and can result in a wide variety of by-products, for example, tri-phenols and tetra-phenols.

In addition to the diffusion issues that arise when using gel-like ion exchange resins, these resins suffer from compressibility issues that arise due to the fluid flow during the reaction. The compressibility issues of the gel-like ion exchange resin limits the flow rate of the feed when used in a down flow reactor, requiring reactors with larger diameters to be used. The compressibility issues of gel-like ion exchange resins limits the flow rate of the feed when used in an up flow reactor due to the fluidization of the catalyst bed.

An improved catalyst for the production of bisphenols, for example, bisphenol A is desirable.

BRIEF SUMMARY

Disclosed herein is a cross-linked polystyrene catalyst, a method of making, and uses thereof.

In an embodiment, a catalyst comprises a porous carrier having 5 to 200 pores per 2.54 centimeters and a pore volume of at least 90 volume percent (vol %) based on the total volume of the porous carrier; wherein the porous carrier comprises one or both of carbon and a metal; and a sulfonated, cross-linked polystyrene located on at least part of a surface of the porous carrier.

In another embodiment, a method of making the catalyst of any one of the preceding claims, comprises polymerizing a polymerization mixture comprising a styrene monomer and a cross-linker in the presence of the porous carrier to form a polystyrene coated porous carrier having a cross-linked polystyrene located on the at least part of the surface of the porous carrier; separating the polystyrene coated porous carrier from the polymerization mixture; further polymerizing the cross-linked polystyrene after the separating; and sulfonating the further polymerized cross-linked polystyrene to form the catalyst.

In an embodiment, the catalyst is used for producing a bisphenol.

In yet another embodiment, a method for producing a bisphenol comprises reacting a phenolic compound with a reactant comprising one or both of an aldehyde and a ketone in the presence of the catalyst to produce the bisphenol.

The above described and other features are exemplified by the following figures and detailed description.

BRIEF DESCRIPTION OF THE DRAWINGS

Refer now to the figures, which are exemplary embodiments.

DETAILED DESCRIPTION

It was surprisingly discovered that a catalyst comprising a porous carrier, for example, a foam carrier, and a sulfonated, cross-linked polystyrene located on at least part of a surface of the porous carrier can be used in the production of bisphenols. While foam supported sulfonated polystyrene catalysts are known in general (V. V. Ordomsky et al., "Foam supported sulfonated polystyrene as a new acidic material for catalytic reactions", Chem. Eng. J. (2012) http://dx-.doi.org/10.1016/j.cej.2012.06.068), such a catalyst had not been used in the production of bisphenols as it was believed that the high acidity of the reaction mixture would deactivate the catalyst. It was surprisingly discovered that when the sulfonated polystyrene was cross-linked, that the catalyst was capable of functioning in the bisphenol reaction. It was further surprisingly discovered that even though the catalyst is located on a porous carrier, the catalyst was not susceptible to the compressibility issues of the gel-like ion exchange resin catalysts.

Specifically, the catalyst comprises a porous carrier that can have one or both of 5 to 200 pores per 2.54 centimeters (1 inch), or 5 to 100 pores per 2.54 centimeters and a pore volume of at least 90 vol %, or 94 to 98 vol % based on the total volume of the porous carrier. The number of pores per unit length can be determined in accordance with ASTM D3576-04 (2010), Procedure A. The pore volume can be determined using the following equation where the pore volume is equal to 1−(foam density/material density). For example, for a foam having a foam density of 40 kilograms per meter cubed ($kg/m^3$) that is made from a foam material of amorphous carbon having a density of 2,000 $kg/m^3$, the pore volume is 0.98 (1−(40/2,000)).

The porous carrier can comprise a carbon porous carrier, for example, an amorphous carbon carrier. The porous carrier can comprise a ceramic porous carrier. The porous carrier can comprise carbon on a metal porous carrier. The metal can comprise aluminum, chromium, iron, copper, silicon (for example, silicon carbide), nickel, or a combination thereof. The metal can comprise stainless steel. The porous carrier can be a foam carrier. Examples of porous carriers include those that are commercially available from ERG Aerospace Corporation, Oakland Calif. and from Alantum Corporation, Gyonggi-Do, Korea.

A sulfonated, cross-linked polystyrene can be located on at least a portion of the surface of the porous carrier. The sulfonated, cross-linked polystyrene can comprise 0.5 to 20 mole percent (mol %), or 1 to 15 mol %, or 1 to 10 mol %, or 1 to 5 mol % of a repeat unit derived from a cross-linker relative to a total amount of repeat units.

The catalyst can have an initial acid content of 0.01 to 0.2 milli-equivalents of acid groups per centimeter cubed of the catalyst. When introduced to a solution comprising phenol, acetone, or a combination thereof at a temperature of 75 degrees Celsius (° C.) for 24 hours, the sulfonated, cross-linked polystyrene can retain at least 75 weight percent (wt %) of the initial acid content.

The sulfonated, cross-linked polystyrene can be grafted onto a thermoplastic layer located on the surface of the porous carrier. The thermoplastic layer can comprise a polycarbonate, a poly(phenylene ether), a polyimide (e.g., polyetherimide), a polybutadiene, a polyacrylonitrile, a poly ($C_{1-12}$ alkyl)methacrylate (e.g., polymethylmethacrylate (PMMA)), a polyester (e.g., poly(ethylene terephthalate), poly(butylene terephthalate), and polythioester), a polyolefin (e.g., polypropylene (PP), high density polyethylene (HDPE), low density polyethylene (LDPE), linear low density polyethylene (LLDPE)), a polyamide (e.g., polyamideimide), a polyarylate, a polysulfone (e.g., polyarylsulfone, polysulfonamide), a poly(phenylene sulfide), a poly(phenylene oxide), a polyether (e.g., poly(ether ketone) (PEK), poly(ether ether ketone) (PEEK), polyethersulfone (PES)), a polyacrylic, a polyacetal, a polybenzoxazoles (e.g., polybenzothiazole, polybenzothiazinophenothiazine), a polyoxadiazole, a polypyrazinoquinoxaline, a polypyromellitimide, a polyquinoxaline, a polybenzimidazole, a polyoxindole, a polyoxoisoindoline (e.g., polydioxoisoindoline), a polytriazine, a polypyridazine, a polypiperazine, a polypyridine, a polypiperidine, a polytriazole, a polypyrazole, a polypyrrolidine, a polycarborane, a polyoxabicyclononane, a polydibenzofuran, a polyphthalide, a polyacetal, a polyanhydride, a vinyl polymer (e.g., a poly(vinyl ether), a poly(vinyl thioether), a poly(vinyl alcohol), a poly(vinyl ketone), a poly(vinyl halide) (for example, poly(vinyl chloride)), a poly(vinyl nitrile), a poly(vinyl ester)), a polysulfonate, a polysulfide, a polyurea, a polyphosphazene, a polysilazane, a polysiloxane, a fluoropolymer (e.g., poly(vinyl fluoride) (PVF), poly(vinylidene fluoride) (PVDF), fluorinated ethylene-propylene (FEP), polytetrafluoroethylene (PTFE), polyethylenetetrafluoroethylene (PETFE)), or a combination thereof. The thermoplastic layer can comprise a polyolefin, for example, polyethylene, polypropylene, or a combination thereof. The thermoplastic layer can comprise polypropylene, for example, isotactic polypropylene.

A method of making the catalyst can comprise polymerizing a polymerization mixture comprising a styrene monomer and a cross-linker in the presence of the porous carrier to form a polystyrene coated porous carrier having a cross-linked polystyrene located on the at least part of the surface of the porous carrier; separating the polystyrene coated porous carrier from the polymerization mixture; further polymerizing the cross-linked polystyrene after the separating; and sulfonating the further polymerized cross-linked polystyrene to form the catalyst.

The polymerization mixture can comprise a styrene monomer and the cross-linker. The styrene monomer can comprise one or both of styrene and a substituted styrene monomer, for example, alpha-methyl styrene, vinyl toluene, ethyl vinyl benzene, vinyl naphthalene, or a combination thereof.

The polymerization mixture can comprise a cross-linker, for example, a polyvinyl monomer, an aliphatic crosslinking monomer, or a combination thereof. The polyvinyl monomer can comprise divinyl benzene, divinyl toluene, trivinyl benzene, divinyl chloro benzene, diallyl phthalate, divinyl naphthalene, divinyl xylene, divinyl ethyl benzene, trivinyl naphthalene, polyvinyl anthracene, or a combination thereof. The aliphatic cross-linking monomer can comprise trivinyl cyclohexane, a di- or polyacrylate or a di- or poly methacrylate (for example, trimethylol propane trimethacrylate, ethylene glycol dimethacrylate, ethylene glycol diacrylate, neopentyl glycol dimethacrylate, and pentaerythritol tetra- and trimethacrylates), or a combination thereof. The cross-linker can be present in an amount of less than or equal to 20 wt %, or 0.01 to 15 wt %, or 1 to 12 wt %, or 1 to 6 wt % based on the total weight of the monomers.

The polymerization mixture can comprise at least one initiator. The initiator can be a free radical initiator. Examples of free radical initiators include oil-soluble initiators, for example, benzoyl peroxide, lauroyl peroxide, t-butyl peroctoate, t-butyl peroxy benzoate, t-butyl peroxy pivalate, t-butylperoxy-2-ethylhexanoate, bis(4-t-butyl cyclohexyl) peroxy dicarbonate, an azo compound (for example, azobisisobutrylonitrile and azobisdimethyl valeronitrile), or a combination thereof. The initiator can comprise two or more initiators. For example, the initiator can comprise a fast acting initiator having a short lifetime and a slow acting initiator having an increased lifetime relative to the fast acting initiator.

The polymerization mixture can further comprise a stabilizer. The stabilizer can comprise gelatin, starch, carboxymethylcellulose, poly(acrylic acid), poly(vinyl alcohol), a water-insoluble inorganic stabilizer in particulate form (for example, bentonite and magnesium hydroxide), or a combination thereof.

The temperature of the polymerization mixture can be increased to a polymerization temperature that is greater than or equal to the activation temperature of the initiator in order to initiate the polymerization reaction. For example, the polymerization temperature can be 40 to 100° C., or 50 to 90° C.

Prior to the polymerizing of the polymerization mixture, a thermoplastic layer can be coated on the porous carrier to form a thermoplastic coated porous carrier. The thermoplastic layer can be coated onto the porous carrier, for example, by introducing (for example, by spray coating or submerging) the porous carrier into a solution comprising the thermoplastic polymer. For example, the porous carrier can be submerged in a solution comprising 1 to 10 wt % of polypropylene based on the total weight of the solution at 90 to 150° C.

Also prior to the polymerizing, the porous carrier and, if present, the thermoplastic layer can optionally be subjected to a plasma treatment, a corona treatment, an ozone treatment, or a combination thereof. Such a treatment can result in the formation of radicals on the surface that can serve to initiate the polymerization reaction, forming a grafted polystyrene.

After polymerization, the polystyrene coated porous carrier can be separated from the suspending medium (for example, by gravity, centrifugal flow, hydraulic separation, or filtration), dried, sulfonated, and functionalized.

After the separating, the polystyrene can be further polymerized. For example, the separated polystyrene coated porous carrier can be heated, for example, to a temperature of greater than or equal to 40° C., or 40 to 100° C., or 50 to 90° C. The heating can occur for greater than or equal to 4 hours, or greater than or equal to 7 hours, or 4 to 20 hours, or 8 to 15 hours.

The sulfonating can comprise introducing a swelling agent to the cross-linked polystyrene to form a swollen polystyrene; introducing a sulfonating agent to the swollen polystyrene to form the sulfonated cross-linked polystyrene; and washing the sulfonated cross-linked polystyrene. The swelling agent can comprise chloroform, 1,2 dichloroethane, tetrahydrofuran, or a combination thereof. The swelling agent can comprise a chlorinated hydrocarbon, for example, chloroform, 1,2 dichloroethane, or a combination thereof. The sulfonating agent can comprise sulfur trioxide, sulfuric acid, or a combination thereof. The sulfonating agent can comprise, for example, a sulfuric acid/SO$_3$ mixture having an acid concentration of 101 to 104.5%, for example, to introduce an average of at least one sulfonic acid group per aromatic nucleus. The sulfonating can be less than or equal to 20 hours, or less than or equal to 15 hours, or 1 to 5 hours.

The sulfonated, cross-linked resin can then be functionalized with a promoter molecule that comprises at least two thiol groups. The sulfonated, cross-linked resin can further be optionally functionalized with a promoter molecule that comprises at least one thiol group. The sulfonated, cross-linked resin can then be functionalized such that the resultant catalyst system comprises 5 to 35 mol %, or 10 to 30 mol %, 10 to 25 mol %, or 15 to 25 mol % of an attached promoter molecule based on the total moles of the sulfonic acid sites in the catalyst system. The sulfonated, cross-linked resin can then be functionalized such that the resultant catalyst system comprises 10 to 20 mol % of an attached promoter molecule based on the total moles of the sulfonic acid sites in the catalyst system.

The attached promoter molecule can have the formula:

wherein a and b are each independently an integer of 0 to 5, $R_n$ can be an amine group, a pyridine group, a phosphonium group, or a $C_{1-4}$ group (for example, a $C_{1-4}$ alkyl group); and $R_1$, $R_2$, $R_3$, and $R_4$ can each independently be —H, —OH, —SH, or an alkyl group (for example, a $C_{1-4}$ group).

The catalyst system can have the formula:

wherein IER is the cross-linked resin; a, b, $R_1$, $R_2$, $R_3$, and $R_4$ are defined above; and $R_n$ is covalently or ionically bound to the sulfonic acid site and can be an amine group, a pyridine group, a phosphonium group, or a $C_{1-4}$ group (a $C_{1-4}$ alkyl group). For example, $R_n$ can be an amine group and $R_1$, $R_2$, $R_3$, and $R_4$ can each be —H.

The method of preparing the catalyst can be performed in an inert environment and under a continuous flow of an inert gas. The inert gas can comprise nitrogen, argon, or a combination thereof.

The catalyst can be used as a fixed-bed catalyst in condensation reactions, for example, the condensation of a phenolic compound with a reactant comprising one or both of a ketone and an aldehyde to produce a bisphenol. The catalyst can be exposed to a feed comprising a condensation mixture comprising the phenolic compound and a reactant comprising one or both of a ketone and an aldehyde. The feed can comprise less than or equal to 2 wt %, or 0 to 2 wt %, or 0 to 1 wt % of water based on the total weight of the feed. The feed can comprise methanol in an amount of 250 to 5,000 parts per million by weight (ppm), or 250 to 4,000 ppm, or 260 to 3,000 ppm, or 260 to 2,000 ppm based on the total weight of the reactant.

The reaction of the phenolic compound and the aldehyde or ketone can occur in a stoichiometric amount or in a molar excess of the phenolic compound. For example, the molar ratio of the phenolic compound to the aldehyde or ketone can be 20:1 to 2:1. The feed can comprise 3 to 15 wt %, or 5 to 10 wt % of the reactants based on the total weight of the feed.

The reaction can occur at a temperature of 40 to 150° C., or 55 to 100° C. with, for example, 1 to 40 wt % catalyst based on the weight of the phenolic compound and the aldehyde or ketone. The reaction can occur at a weight hourly space velocity (WHSV) of 0.2 to 30 inverse hours (hr$^{-1}$), or 0.5 to 20 hr$^{-1}$.

The ketone can have the formula $R^{k1}$—(C=O)—$R^{k2}$, wherein $R^{k1}$ and $R^{k2}$ can each independently be a $C_{1-18}$, or a $C_{1-6}$ aliphatic group, and can comprise heteroatoms, for example, one or more of halogens, oxygen, nitrogen, sulfur, silicon, and phosphorous provided that such substituents do not substantially adversely affect the reaction or reaction product. $R^{k1}$ and $R^{k2}$ can together form a $C_{5-18}$ cycloalkyl group (for example, cyclohexanone or methylcyclohexanone) or a $C_{5-18}$ cycloalkylene group. The aldehyde can have the formula $R^{k1}$—(C=O)—H, wherein $R^{k1}$ can be that described above or hydrogen.

A wide variety of phenolic compounds can be used, which, as used herein means an aromatic compound substituted with a single hydroxyl group. The aromatic compound can be monocyclic or polycyclic, and can be substituted with up to 5 substituents, provided that such substituents do not substantially adversely affect the reaction or reaction product.

The method can result in the formation of a bisphenol of the formula HO—$R^1$—OH, wherein the $R^1$ group can contain an aliphatic, an alicyclic, or an aromatic moiety. For example, the bisphenol can have the formula (2)

HO-$A^1$-$Y^1$-$A^2$-OH     (2)

wherein each of $A^1$ and $A^2$ is a monocyclic divalent aromatic group and $Y^1$ is a single bond or a bridging group having one or more atoms that separate $A^1$ from $A^2$. One atom can separate $A^1$ from $A^2$.

The bisphenol can have the formula (3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically, para) to each other on the $C_6$ arylene group. The bridging group $X^a$ can be single bond, —O—, —S—, —S(O)—, —S(O)$_2$—, —C(O)—, or a $C_{1-18}$ organic group. The $C_{1-18}$ organic bridging group can be cyclic or acyclic, aromatic or non-aromatic, and can further comprise heteroatoms, for example, halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. p and q can each be 1, and $R^a$ and $R^b$ are each a $C_{1-3}$ alkyl group, for example, methyl, disposed meta to the hydroxy group on each arylene group.

$X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Groups of this type include methylene, cyclohexylmethylene, ethylidene, neopentylidene, isopropylidene, 2-[2.2.1]-bicycloheptylidene, cyclohexylidene, cyclopentylidene, cyclododecylidene, and adamantylidene.

$X^a$ can be a $C_{1-18}$ alkylene group, a $C_{3-18}$ cycloalkylene group, a fused $C_{6-18}$ cycloalkylene group, or a group of the formula -$B^1$-G-$B^2$- wherein $B^1$ and $B^2$ are the same or different $C_{1-6}$ alkylene group and G is a $C_{3-12}$ cycloalkylidene group or a $C_{6-16}$ arylene group. For example, $X^a$ can be a substituted $C_{3-18}$ cycloalkylidene of formula (4)

wherein $R^r$, $R^p$, $R^q$, and $R^t$ are each independently hydrogen, halogen, oxygen, or $C_{1-12}$ hydrocarbon groups; Q is a direct bond, a carbon, or a divalent oxygen, sulfur, or —N(Z)— where Z is hydrogen, halogen, hydroxy, $C_{1-12}$ alkyl, $C_{1-12}$ alkoxy, or $C_{1-12}$ acyl; r is 0 to 2, t is 1 or 2, q is 0 or 1, and k is 0 to 3, with the proviso that at least two of $R^r$, $R^p$, $R^q$, and $R^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is one and q is 0, the ring as shown in formula (4) contains 4 carbon atoms, when k is 2, the ring as shown in formula (4) contains 5 carbon atoms, and when k is 3, the ring contains 6 carbon atoms. Two adjacent groups (e.g., $R^q$ and $R^t$ taken together) can form an aromatic group or $R^q$ and $R^t$ taken together can form one aromatic group and $R^r$ and $R^p$ taken together form a second aromatic group. When $R^q$ and $R^t$ taken together form an aromatic group, $R^p$ can be a double-bonded oxygen atom, i.e., a ketone.

Specific examples of bisphenol compounds of formula (3) include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds can also be used. The polycarbonate can be a linear homopolymer derived from bisphenol A, in which each of $A^1$ and $A^2$ can be p-phenylene, and $Y^1$ can be isopropylidene in formula (3).

The catalyst system can be used in the condensation of cyclohexanone and o-cresol to produce 1,1-bis(4-hydroxy-3-methylphenyl) cyclohexane (DMBPC).

The catalyst system can be used in the condensation of acetone and phenol to produce BPA.

After formation of the bisphenol, the product mixture can be post-treated to purify the bisphenol. The post-treatment can comprise crystallization of bisphenol to form crystals comprising a crystallized bisphenol and/or a crystallized bisphenol adduct. The crystallization can comprise a vacuum cooling step. The crystallization can be facilitated by adding water, for example, in an amount of less than or equal to 3 wt %, or 0.1 to 3 wt % based on the total weight of the product mixture. The crystals can be optionally separated, for example, by filtration and melted in a melting unit. If the melt comprises sulfur, then a base (for example, sodium hydroxide and potassium hydroxide) can be added to the melt to form a melt stream with a reduced sulfur content. The melted stream can be filtered, further purified, and then solidified, for example, in a flaking unit.

The bisphenols produced by this process can be used to manufacture a polycarbonate. A "polycarbonate" as used herein means compositions having repeating structural carbonate units of formula (1)

(1)

in which the $R^1$ groups contain aliphatic, alicyclic, and/or aromatic moieties (e.g., greater than or equal to 30%, or greater than or equal to 60%, of the total number of $R^1$ groups can contain aromatic moieties and the balance thereof are aliphatic or alicyclic). Optionally, each $R^1$ can be a $C_{6-30}$ aromatic group, that is, can contain at least one aromatic moiety. $R^1$ can be derived from the bisphenol.

The following non-limiting examples further illustrate the various embodiments described herein. The examples are merely illustrative and are not intended to limit devices made in accordance with the disclosure to the materials, conditions, or process parameters set forth therein.

EXAMPLES

Example 1: Preparation of a Catalyst with an Uncross-Linked Polystyrene

A foam catalyst was provided by Technical University Eindhoven following the procedure of Chem. Engr. J., 2012, http://dx.doi.org/10.1016/j.cej.2012.06.068. The initial foam was prepared by sulfonating an uncross-linked polystyrene that was grafted onto a polypropylene layer located on a carbon foam. The polypropylene layer was predeposited by melting a polypropylene powder onto the surface of the carbon foam. The sulfonating was performed by chlorosulfonic acid such that the initial foam sample contained 0.42 millimoles (mmol) of acid sites per gram (g) of the foam catalyst.

The stability of the foam catalyst was then determined by exposing the catalyst to a solution of phenol comprising 6 wt % acetone based on the total weight of the solution for 48 hours (hr). After exposure, visual observation using a light microscope of the surface of the foam indicated that the foam layer was free of the catalyst layer and the color of the solution had changed. The exposed foam had a 21% weight loss relative to the initial foam catalyst and had 0 mmol of acid sites per gram of foam; in other words, the catalyst layer was confirmed to be completely removed.

Example 2: Preparation of a Catalyst with a Cross-Linked Polystyrene

A carbon foam having 20 pores per inch and a pore volume of 93-98 vol % immersed in a mixture of 94.4 wt % of a styrene monomer, 3 wt % of divinylbenzene, 1.4 wt % of benzoylperoxide, 0.8 wt % of azobisisobutyronitrile, and 0.4 wt % of dimethylaniline in a round bottom flask. The mixture was continuously stirred in a closed nitrogen environment. The flask had a condenser on top to reflux any material that evaporated. The mixture was heated to 70° C. for 1 hour.

The excess liquid was removed from the foam leaving behind a film of low molecular weight polystyrene under nitrogen and the foam was dried in an oven at atmospheric pressure and a temperature of 70° C. for 8 hours. During the drying, the remaining benzoylperoxide and azobisisobutyronitrile further polymerized the low molecular weight polystyrene to form a high molecular weight polystyrene. The polystyrene coated carbon foam had a weight increase of 30 wt % relative to the weight of the initial carbon foam.

The polystyrene coated foam was then introduced to a swelling solution of dichloromethane (DCM) for 3 hours and then to a sulfonation solution comprising 9 vol % of chlorosulfonic acid (CSA) in dichloromethane for 1 hour at room temperature (23° C.). The excess solution was then removed and the foam was introduced to a solution comprising 95 to 98 wt % of sulfuric acid in an ice bath. Water was slowly added to dilute the sulfuric acid. The foam sample was then washed with demineralized water until a pH of the rinse water was the same as the pH of the initial demineralized water.

As is shown in Table 1, the resultant catalyst contained 0.054 milli-equivalent of acid groups per centimeter cubed ($cm^3$). It is noted that it is expected that had these experiments been performed under a constant flow of nitrogen as opposed to merely being in a closed nitrogen environment, that the acid groups after the stability testing would have been higher. Without being bound by theory, it is believed that the reaction environment contained an amount of oxygen that reduced the amount of cross-linking.

TABLE 1

| Example | 2 | 3 | 4 | 5 |
|---|---|---|---|---|
| Pores (ppi) | 20 | 20 | 20 | 20 |
| PP layer | No | No | No | No |
| Divinylbenzene (wt %) | 3 | 3 | 5 | 10 |
| Swelling agent | DCM | DCM | DCM | DCM |
| Swelling time (hr) | 3 | 24 | 24 | 24 |
| Sulfonating agent/solvent | CSA/DCM | CSA/DCM | CSA/DCM | CSA/DCM |
| Initial acid groups (milli-equivalent of acid groups per $cm^3$) | 0.054 | 0.040 | 0.033 | 0.023 |
| Acid groups after stability test (milli-equivalent of acid groups per $cm^3$) | 0.040 | 0.009 | 0.014 | 0.002 |

Examples 3-5: Effect of Varying the Swelling Time and the Cross-Link Density

Three catalysts were prepared according to the procedure of Example 2 except that the amount of divinylbenzene was varied from 3, 5, and 10 wt %, respectively; the amount of styrene was 94.4, 92.4, and 87.4 wt %; and the exposure time to the dichloromethane was increased to 24 hours.

The resultant catalysts contained 0.040, 0.033, and 0.023 milli-equivalent acid groups per $cm^3$, respectively, as is shown in Table 1. Table 1 shows that increasing the amount of cross-linking in Examples 3-5 results in a decrease in the amount of the initial acid sites. Table 1 further shows that, when comparing Examples 2 and 3, increasing the swelling time in the dichloromethane results in a reduction in the amount of initial acid groups.

Example 6: Preparation of a Catalyst with a Cross-Linked Polystyrene

A carbon foam having 20 pores per inch and a pore volume of 93 to 98 vol % was immersed in a mixture of 94.4 wt % of a styrene monomer, 3 wt % of divinylbenzene, 1.4 wt % of benzoylperoxide, 0.8 wt % of azobisisobutyronitrile, and 0.4 wt % of dimethylaniline in a round bottom flask. The mixture was continuously stirred in a closed nitrogen environment with a continuous nitrogen flow. The flask had a condenser on top to reflux any material that evaporated. The mixture was heated to 70° C. for 1 hour.

The excess liquid was removed from the foam leaving behind a film of low molecular weight polystyrene under nitrogen and the foam was dried in an oven at atmospheric pressure and a temperature of 70° C. for 8 hours. During the drying, the remaining benzoylperoxide and azobisisobutyronitrile further polymerized the low molecular weight polystyrene to form a high molecular weight polystyrene. The polystyrene coated carbon foam had a weight increase of 30 wt % relative to the weight of the initial carbon foam.

The polystyrene coated foam was then introduced to a swelling solution of chloroform (CF) for 2 hours and then to a sulfonation solution comprising 9 vol % of chlorosulfonic acid in chloroform for 1 hour at room temperature. The excess solution was then removed and the foam was introduced to a solution comprising 95 to 98 wt % of sulfuric acid in an ice bath. Water was slowly added to dilute the sulfuric acid. The foam sample was then washed with demineralized water until a pH of the rinse water was the same as the pH of the initial demineralized water.

As is shown in Table 2, the resultant catalyst contained 0.036 milli-equivalent of acid groups per $cm^3$.

Table 2 shows that the resultant catalyst contained 0.045 milli-equivalent acid groups per $cm^3$ illustrating that THF is a good swelling agent.

Example 9: Effect of Using a Toluene Swelling Agent

A catalyst was prepared according to the procedure of Example 6 except that the polystyrene coated foam was introduced to a swelling solution of toluene (TOL) for 2 hours and then to a sulfonation solution comprising 9 vol % of chlorosulfonic acid in toluene for 1 hour at room temperature. The amounts of initial acid groups are shown in Table 2.

Table 2 shows that the resultant catalyst only contained 0.001 milli-equivalent acid groups per $cm^3$ illustrating that toluene is not a good swelling agent.

Example 10: Preparation of a Porous Carrier Catalyst with a Grafted Polystyrene A carbon foam having 20 pores per inch was coated with an isotactic polypropylene (PP) having a weight average

TABLE 2

| | Example | | | | | |
|---|---|---|---|---|---|---|
| | 6 | 7 | 8 | 9 | 10 | 12 |
| Pores (ppi) | 20 | 20 | 20 | 20 | 20 | 45 |
| PP layer | No | No | No | No | Yes | Yes |
| Divinylbenzene (wt %) | 3 | 3 | 3 | 3 | 3 | 3 |
| Swelling agent | CF | CF | THF | TOL | DCM | DCM |
| Swelling time (hr) | 2 | 2 | 2 | 2 | 3 | 3 |
| Sulfonating agent/solvent | CSA/ CF | CSA/ CF | CSA/ DCM | CSA/ TOL | CSA/ DCM | CSA/ DCM |
| Initial acid groups (milli-equivalent of acid groups per $cm^3$) | 0.036 | 0.079 | 0.045 | 0.001 | 0.020 | 0.123 |
| Acid groups after stability test (milli-equivalent of acid groups per $cm^3$) | 0.038 | 0.055 | 0.046 | 0 | 0.024 | 0.120 |

Example 7: Effect of Increasing the Amount of Catalytic Layer on the Support A catalyst was prepared according to the procedure of Example 6 except that the mixture was heated at 70° C. for 2 hours, resulting in approximately 3 times more cross-linked polystyrene on the porous carrier as established by the weight increase of the foam catalysts relative to the weight of the respective initial carbon foams.

As is shown in Table 2, the catalyst Example 7 contained significantly more acid groups as compared to the catalyst of Example 6, 0.079 milli-equivalent acid groups per $cm^3$ and compared to 0.036 milli-equivalent acid groups per $cm^3$. Without being bound by theory, it is believed that the catalyst of Example 7 contained more acid groups because of the increased amount of cross-linked polystyrene material present in the catalyst.

Example 8: Effect of Using a THF Swelling Agent

A catalyst was prepared according to the procedure of Example 6 except that the polystyrene coated foam was introduced to a swelling solution of tetrahydrofuran (THF) for 2 hours and then to a sulfonation solution comprising 9 vol % of chlorosulfonic acid in DCM for 1 hour at room temperature. The amount of initial acid groups is shown in Table 2.

molecular weight of 250,000 grams per mole (g/mol) based on polystyrene standards. The polypropylene was coated by introducing the foam to a homogeneous solution comprising 1 to 1.2 grams of polypropylene, 8 milliliters (mL) of methyl ethyl ketone (MEK), and 40 mL of xylene at 120° C. After wetting, the foams were removed from the solution and placed in a vacuum at 90° C. for 1 hour or until the foam appeared white, indicating that the polypropylene was no longer swollen with solvent. Typically, the presence of the polypropylene layer resulted in a weight increase of the initial foam of 10% relative to the initial weight of the foam.

The catalyst was then prepared according to the procedure of Example 6 except that the polypropylene coated foam was used instead of the untreated foam, the coated foam was introduced to a swelling solution of DCM for 3 hours, and then to a sulfonation solution comprising 9 vol % of chlorosulfonic acid in DCM for 1 hour at room temperature.

The coated carbon foam had a weight increase of 27 weight percent relative to the weight of the polypropylene coated carbon foam (309 milligrams from 244 milligrams) and an acid content of 0.020 milli-equivalent acid groups per $cm^3$ as is shown in Table 2.

Example 11: Effect of Multiple Deposition Steps in the Polypropylene Solution A carbon foam having 20 pores per inch was dipped 5 separate times into the polypropylene solution of Example 10. After each exposure, the foam sample was placed in a vacuum at 90° C. for 1 hour or until the foam appeared white. The weight increase relative to the initial foam after each exposure was: 8 wt %, 18 wt %, 29 wt %, 48 wt %, and 65 wt %, respectively. These results illustrate that the amount of the polypropylene deposited can be controlled by increasing or decreasing the amount of times the foam is introduced to the polypropylene solution.

Example 12: Effect of Changing Pore Size

Five catalysts were prepared according to the procedure of Example 10 except that carbon foam samples having 45 pores per inch and an initial weight of 313 milligrams each were used. The final catalysts each weighed on average 623 milligrams and had an acid content on average of 0.123 milli-equivalent acid groups per $cm^3$, both of which are averages of the final weight and the final acid contents of the five catalyst samples, respectively.

Comparing Examples 10 and 12, Table 2 shows that increasing the number of pores per inch resulted in a significant increase in the initial acid groups.

Example 13: Stability Testing of the Catalysts of Examples 2-10 and 12

Stability tests were performed on the catalysts of Examples 2-10 and 12, where the catalysts were introduced to a solution of acetone and phenol having a weight ratio of 10:90 for 5 hours at 70° C. The amounts of acid groups after the stability tests are shown in Tables 1 and 2.

The catalyst of Example 10 was then subjected to two further stability tests. As is shown in Table 2, the acid content after the first stability test was 0.024 milli-equivalent acid groups per $cm^3$. The acid contents after the second and third stability tests were 0.033 and 0.041 milli-equivalent acid groups per $cm^3$, respectively. According to these results, there was an increase in the number of active sites with increased exposure to the acetone, phenol solution.

Table 1 shows that the stability of the catalysts of Examples 2-5 was not great as compared to the stability of the catalysts of Examples 6-10 and 12. It is believed that the reduced stability of these catalysts is due to an amount of oxygen present during the polystyrene polymerization resulting in a reduced cross-linking. It is further believed that had these examples been performed under a constant flow of nitrogen, then the stability results would be greatly improved.

Table 2 also confirms that toluene is not a good swelling agent as the catalyst contained 0 milli-equivalent acid groups per $cm^3$ after the stability test.

Example 14: BPA Formation Using a Commercial Catalyst in a Batch Reactor

BPA was produced by adding 190 g of phenol, 10 g of acetone, and 4.2 g of dried catalyst to a 1,000 mL double walled glass reactor that was maintained at 70° C. under stirring. The vapor overhead above the liquid was flushed with nitrogen to maintain an inert environment and the vapor outlet was directed to a condenser at 7° C. to prevent loss of acetone. The catalyst used was the AMBERLYST™123 catalyst that is commercially available from The Dow Chemical Company. Prior to use, the catalyst was pre-swollen in phenol for 12 hours and dried in a vacuum oven at 95° C. for 24 hours. The catalyst had an acid content of 5 milli-equivalent acid per g dry catalyst resulting in a total acid content of 21 milli-equivalent acid that was present in the reaction mixture.

After set intervals, samples were taken to measure acetone conversion by titration and p,p-BPA and o,p-BPA formation using high performance liquid chromatography (HPLC). The reaction was monitored for 500 minutes. No mercapto co-promoter was added.

Figure 1:
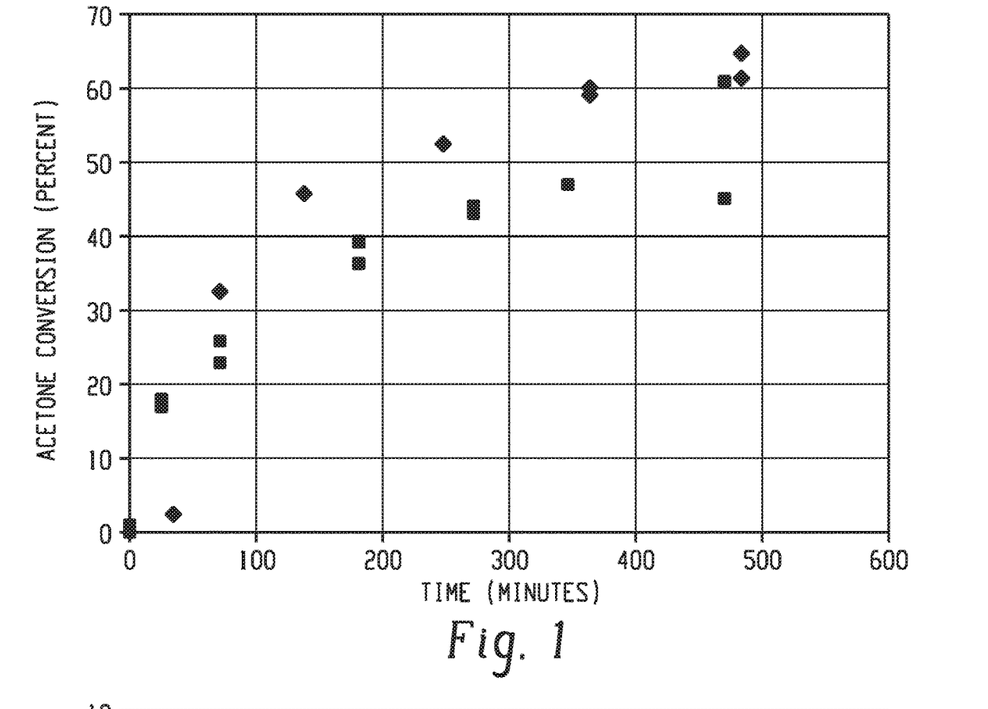
FIG. 1 is a graphical illustration of acetone conversion with time of Example 15.
Figure 2:
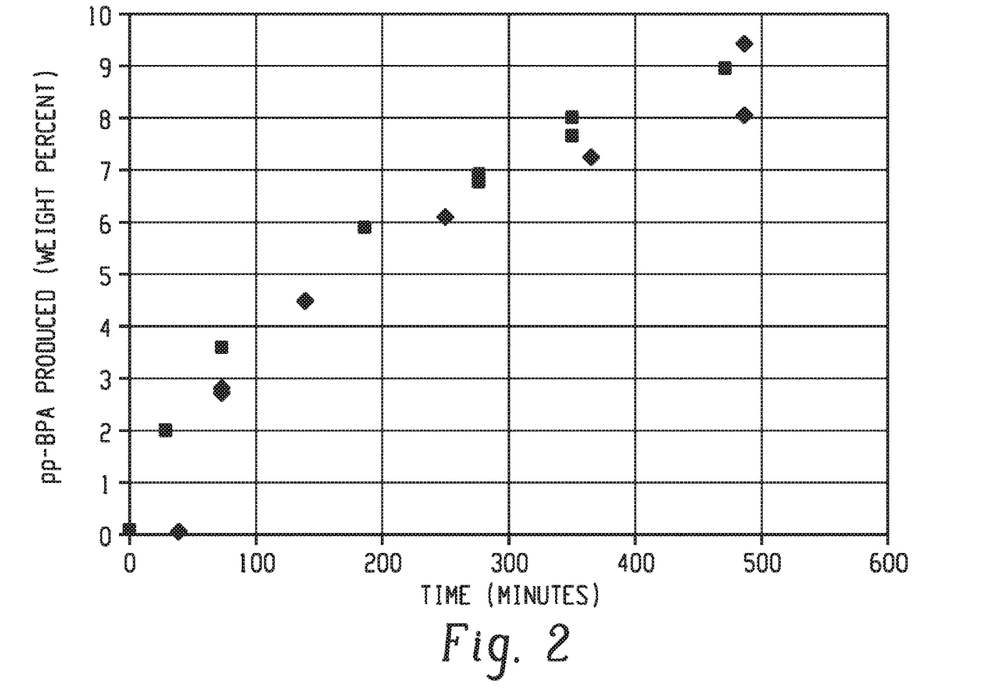
FIG. 2 is a graphical illustration of p,p-BPA production with time of Example 15.
Figure 3:
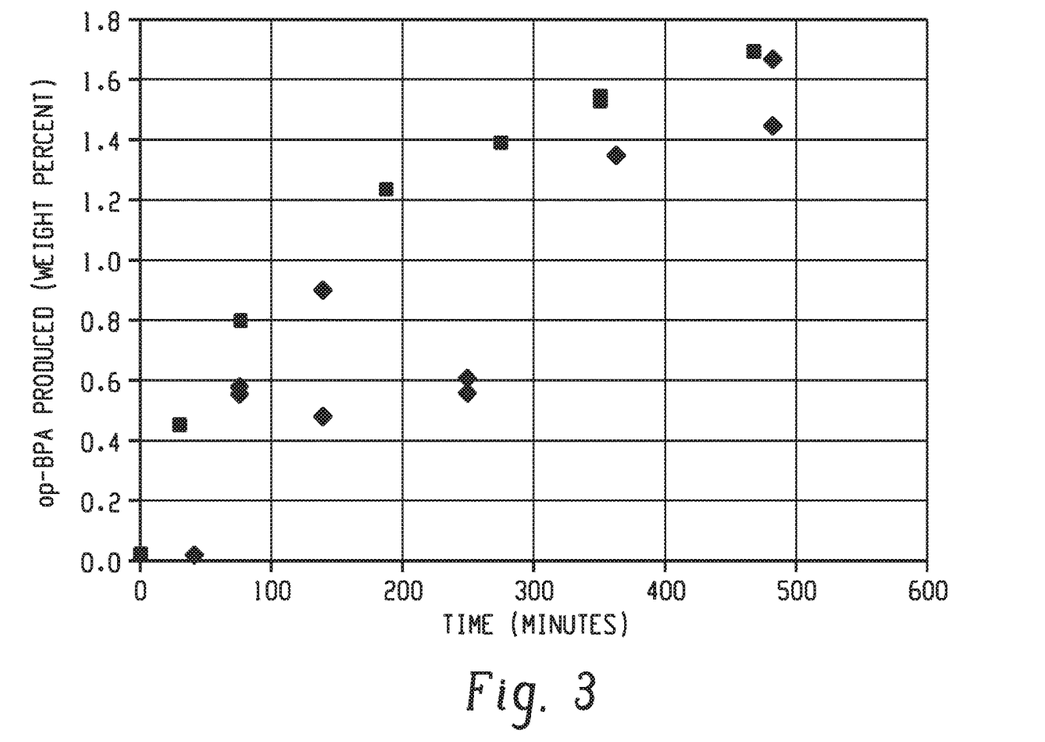
FIG. 3 is a graphical illustration of o,p-BPA production with time of Example 15.

The acetone conversion, p,p-BPA production, and the o,p-BPA production with time for this reaction are illustrated by the diamonds in FIG. 1, FIG. 2, and FIG. 3, respectively.

As is shown in Table 3, after 500 minutes the acetone conversion was 60 wt % and HPLC analysis showed that the mixture contained 9 wt % p,p-BPA and 1.6 wt % o,p-BPA. The amount of p,p-BPA produced per unit of acid after 500 minutes was 0.429 wt % per milli-equivalent acid.

TABLE 3

| | Example | | | | | | |
|---|---|---|---|---|---|---|---|
| | 14 | 15 | 16 | 17 | 18 | 19 | 20 |
| Pores (ppi) | — | 20 | 20 | 20 | 20 | 20 | 45 |
| PP layer | — | N | N | N | Y | Y | Y |
| Divinylbenzene (wt %) | — | 3 | 3* | 3 | 3 | 3 | 3 |
| Swelling agent | — | DCM | DCM | CF | DCM | DCM | CF |
| Swelling time (hr) | — | 3 | 3 | 3 | 3.5 | 5 | 2 |
| Sulfonating agent/solvent | — | CSA/DCM | CSA/DCM | CSA/CF | CSA/DCM | CSA/DCM | CSA/CF |
| Initial acid groups per $cm^3$ of catalyst | — | 0.042 | 0.017 | 0.079 | 0.017 | 0.016 | 0.123 |
| Initial acid groups (milli-equivalents) | 21 | 1.055 | 0.427 | 1.984 | 0.427 | 0.402 | 6.180 |
| p,p-BPA formation (wt %) | 9.0 | 0.21 | 0.14 | 0.76 | 0.19 | 0.26 | 2.20 |
| p,p-BPA formation per milli-equivalent acid (wt %/meq-$H^+$)) | 0.429 | 0.199 | 0.328 | 0.383 | 0.445 | 0.647 | 0.356 |

*Polymerization performed with a solvent of 10 wt % DCM

Example 15: BPA Formation Using a Catalyst with a Deposited Polystyrene in a Batch Reactor BPA was produced using a catalyst with a deposited polystyrene. The catalyst was prepared according to the procedure of Example 6, the foam had 20 pores per inch, the coated foam was introduced to a swelling solution of DCM for 3 hours, and then to a sulfonation solution comprising 9 vol % of chlorosulfonic acid in DCM for 1 hour at room temperature. The catalyst had an initial acid content of 0.042 milli-equivalent acid groups per $cm^3$. As four foam cylinders having a diameter of 2 centimeters (cm) and a height of 2 cm were added to the reactor, there was a total of 1.055 milli-equivalent acid groups present during the reaction.

The reactor was loaded similar to Example 14 with 190 g phenol and 10 g acetone. After set intervals, samples were taken to measure acetone conversion and p,p-BPA and o,p-BPA formation. The reaction was monitored for 500 minutes. No mercapto co-promoter was added.

The acetone conversion, p,p-BPA production, and the o,p-BPA production with time for this reaction are illustrated by the squares in FIG. 1, FIG. 2, and FIG. 3, respectively.

As is shown in Table 3, after 500 minutes the HPLC analysis showed that the amount of p,p-BPA produced per unit of acid was 0.199 wt % per milli-equivalent acid.

Example 16: Effect of DCM Solvent During Polymerization on BPA Formation Using a Catalyst with a Deposited Polystyrene BPA was produced using a catalyst with a deposited polystyrene. The catalyst was prepared according to the procedure of Example 15 except that polymerization was done with 10 wt % DCM as solvent. The catalyst had an initial acid content of 0.017 milli-equivalent acid groups per $cm^3$.

The BPA reaction was performed according to Example 15. As is shown in Table 3, after 500 minutes, the p,p-BPA formation was 0.14 wt % or 0.328 wt % per milli-equivalent acid. In comparing Examples 15 and 16, Table 3 illustrates that adding DCM solvent during polymerization results in an decrease in p,p-BPA formation per milli-equivalent acid.

Example 17: Effect of Swelling Agent During Sulfonation on BPA Formation Using a Catalyst with a Deposited Polystyrene BPA was produced using a catalyst with a deposited polystyrene. The catalyst was prepared according to the procedure of Example 7 except that the swelling agent was chloroform instead of DCM. The catalyst had an initial acid content of 0.079 milli-equivalent acid groups per $cm^3$.

The BPA reaction was performed according to Example 15. As is shown in Table 3, after 500 minutes, the p,p-BPA formation was 0.76 wt % or 0.383 wt % per milli-equivalent acid. In comparing Examples 15 and 17, Table 3 illustrates that using chloroform as the swelling agent results in an increase in p,p-BPA formation per milli-equivalent acid.

Example 18: BPA Formation Using a Catalyst with a Grafted Polystyrene

BPA was produced using a catalyst with a grafted polystyrene. The catalyst was prepared according to the procedure of Example 10 except that the swelling time was 3.5 hours. The foam contained 0.017 milli-equivalent acid groups per $cm^3$.

The BPA reaction was performed according to Example 15. As is shown in Table 3, after 500 minutes the p,p-BPA formation was 0.19 wt % or 0.445 wt % per milli-equivalent acid. In comparing Examples 15-17 with Example 18, Table 3 illustrates that using a catalyst with the grafted polystyrene can result in an increase in p,p-BPA per milli-equivalent acid.

Example 19: Effect of Swelling Time on BPA Formation Using a Catalyst with a Grafted Polystyrene BPA was produced using a catalyst with a grafted polystyrene. The catalyst was prepared according to the procedure of Example 10 except that the swelling time was 5 hours. The foam contained 0.017 milli-equivalent acid groups per $cm^3$.

The BPA reaction was performed according to Example 15. As is shown in Table 3, after 500 minutes the p,p-BPA formation was 0.26 wt % or 0.647 wt % per milli-equivalent acid. In comparing Examples 18 and 19, Table 3 illustrates that increasing the swelling time can result in an increase in p,p-BPA per milli-equivalent acid.

Example 20: Effect of Swelling Solvent on BPA Formation Using a Catalyst with a Grafted Polystyrene BPA was produced using a catalyst with a grafted polystyrene. The catalyst was prepared according to the procedure of Example 10 except that the foam had 45 pores per inch, the swelling solvent was chloroform, and the swelling time was 2 hours. The catalyst had an initial acid content of 0.123 milli-equivalent acid groups per $cm^3$.

The BPA reaction was performed according to Example 15 except that 8 foam catalysts, 285 g of phenol, and 15 g of acetone were added to the reactor. After 500 minutes, Table 3 shows that the p,p-BPA formation was 2.20 wt % or 0.356 wt % per milli-equivalent acid.

Example 21: BPA Formation Using a Commercial Catalyst in a Continuous Reactor BPA was produced by continuously feeding a fixed bed reactor with a reaction mixture of phenol with 6 wt % acetone and 0.31 wt % 3-mercapto-propionic acid. The reactor was a double-wall, continuous reactor having a diameter of 2 cm and an internal height of 30 cm and was maintained at an isothermal temperature of 75° C. The reactor was preloaded with 3.12 g of dried LEWATI™ K1131S catalyst that is commercially available from LANXES™. Prior to use, the catalyst was pre-swollen in phenol for 12 hours and dried in a vacuum oven at 95° C. for 24 hours. The dried catalyst had an acid content of 5.1 milli-equivalent acid per g dry catalyst, resulting in a total acid content of 15.94 milli-equivalent acid that was present in the reaction mixture. The reaction was maintained and monitored for 200 hrs.

The initial p,p-BPA concentration was 13.2 wt % and the p,p-BPA concentration after 185 hours was 10.6 wt %, with an accumulative p,p-BPA production of 290 g. The initial acetone conversion per unit of acid was 0.228 g acetone per milli-equivalent acid and after 185 hours 0.183 g acetone per milli-equivalent acid. The average p,p-BPA:o,p-BPA ratio was 18.7 and the average p,p-BPA selectivity 93.5 wt %. The average by-product formation was 5.0 wt % o,p-BPA and 1.5 wt % other isomers.

Figure 4:
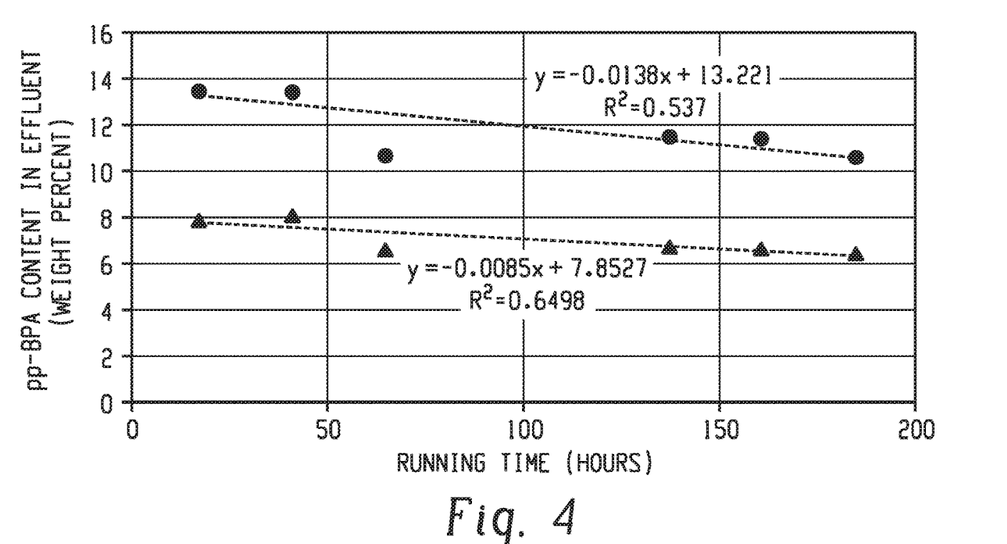
FIG. 4 is a graphical illustration of the p,p-BPA formation with time of Example 21.
Figure 5:
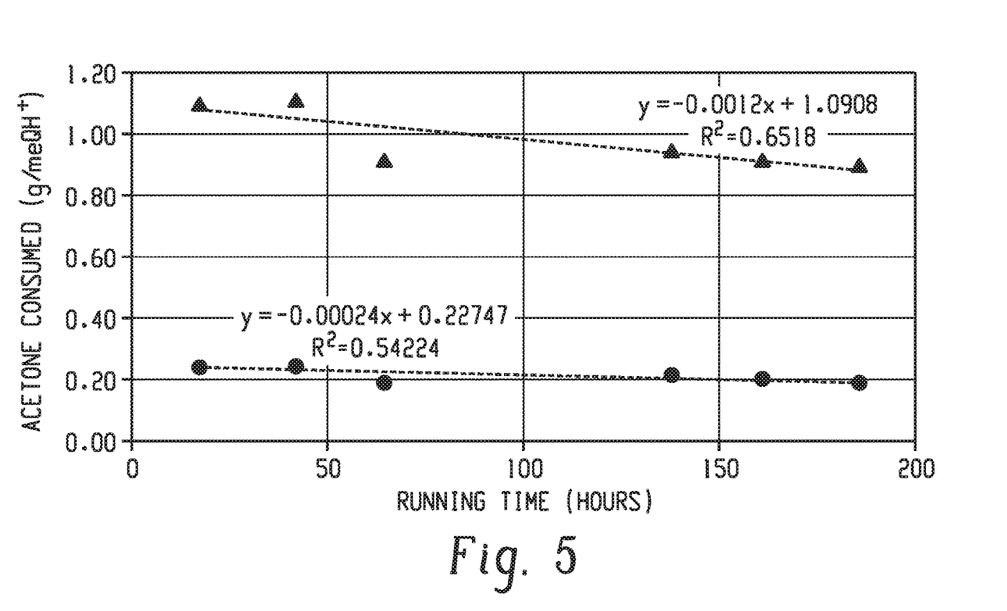
FIG. 5 is a graphical illustration of acetone conversion per unit of acid with time of Example 21.

As is illustrated by the circles, the p,p-BPA formation and the acetone conversion per unit of acid are shown with time in FIG. 4 and FIG. 5, respectively, where g/meQH$^+$ is grams of acetone per milli-equivalents of H.

Example 22: BPA Formation Using a Catalyst with a Grafted Polystyrene in a Continuous Reactor BPA was produced using a catalyst with a grafted polystyrene. The catalyst was prepared according to Example 20. The BPA reaction was performed according to Example 21 except that 5 foam samples were loaded into the reactor for a total acid content of 1.92 milli-equivalent acid.

The initial p,p-BPA concentration was 7.85 wt % and the p,p-BPA concentration after 185 hours was 6.42 wt %, with an accumulative p,p-BPA production of 183 g. The initial acetone conversion per unit of acid was 1.09 g acetone per milli-equivalent acid and after 185 hours 0.90 g acetone per milli-equivalent acid. The average p,p-BPA:o,p-BPA ratio was 30.1 and the average p,p-BPA selectivity 95.9 wt %. The average by-product formation was 3.2 wt % o,p-BPA and 0.9 wt % other isomers.

As is illustrated by the triangle, the p,p-BPA formation and the acetone conversion per unit of acid are shown with time in FIG. 4 and FIG. 5, respectively. FIG. 4 and FIG. 5 illustrate that there is an increased acetone consumption using the foam catalyst with the grafted polystyrene as compared to the commercial catalyst.

Set forth below are non-limiting embodiments of the present disclosure.

Embodiment 1

A catalyst comprising: a porous carrier having 5 to 200 pores per 2.54 centimeters and a pore volume of at least 90 vol % based on the total volume of the porous carrier; wherein the porous carrier comprises one or both of carbon and a metal; and a sulfonated, cross-linked polystyrene located on at least part of a surface of the porous carrier. The porous carrier can have 5 to 100 pores per 2.54 centimeters. The porous carrier can have a pore volume of 94 to 98 vol % based on the total volume of the porous carrier Embodiment 2

The catalyst of Embodiment 1, wherein the sulfonated, cross-linked polystyrene is grafted onto a thermoplastic layer located on the surface of the porous carrier.

Embodiment 3

The catalyst of any one of the preceding embodiments, wherein the sulfonated, cross-linked polystyrene comprises 0.5 to 20 mol % of a repeat unit derived from a cross-linker relative to a total amount of repeat units.

Embodiment 4

The catalyst of any one of the preceding embodiments, wherein the catalyst has an initial acid content of 0.01 to 0.2 milli-equivalents of acid groups per cm$^3$ of the catalyst.

Embodiment 5

The catalyst of Embodiment 4, wherein, when introduced to a solution comprising phenol, acetone, or a combination thereof at a temperature of 75° C. for 24 hours, the sulfonated, cross-linked polystyrene retains at least 75 wt % of the initial acid content.

Embodiment 6

A method of making the catalyst of any one of the preceding embodiments, comprising: polymerizing a polymerization mixture comprising a styrene monomer and a cross-linker in the presence of the porous carrier to form a polystyrene coated porous carrier having a cross-linked polystyrene located on the at least part of the surface of the porous carrier; separating the polystyrene coated porous carrier from the polymerization mixture; further polymerizing the cross-linked polystyrene after the separating; and sulfonating the further polymerized cross-linked polystyrene to form the catalyst.

Embodiment 7

The method of Embodiment 6, further comprising coating the porous carrier with a thermoplastic layer prior to the polymerizing.

Embodiment 8

The method of any one of Embodiments 6 to 7, wherein the polymerization mixture comprises at least one thermal initiator.

Embodiment 9

The method of any one of Embodiments 6 to 8, further comprising plasma treating, corona treating, or ozone treating the porous carrier prior to the polymerizing.

Embodiment 10

The method of any one of Embodiments 6 to 9, wherein the cross-linker is present in the polymerization mixture in an amount of 0.5 to 20 mol % based on the total moles of cross-linker and styrene monomer. The cross-linker can be present in the polymerization mixture in an amount of 2 to 4 mol % based on the total moles of cross-linker and styrene monomer Embodiment 11

The method of any one of Embodiments 6 to 10, wherein the sulfonating comprises introducing a swelling agent to the further polymerized cross-linked polystyrene to form a swollen polystyrene; introducing a sulfonating agent to the swollen polystyrene to form the sulfonated cross-linked polystyrene; and washing the sulfonated cross-linked polystyrene. The swelling agent can comprise a chlorinated hydrocarbon, for example, chloroform, 1,2 dichloroethane, or a combination thereof. The sulfonating agent can comprise sulfur trioxide, sulfuric acid, or a combination thereof.

Embodiment 12

The method of any one of Embodiments 6 to 11, wherein the method is performed in an inert environment and under a flow of an inert material. The inert material can comprise or consist of nitrogen.

Embodiment 13

Use of the catalyst of any one of the preceding embodiments for producing a bisphenol.

Embodiment 14

A method for producing a bisphenol comprising reacting a phenolic compound with a reactant comprising one or both of an aldehyde and a ketone in the presence of the catalyst of any one of Embodiments 1 to 12 to produce the bisphenol.

Embodiment 15

The method of Embodiment 14, wherein the phenolic compound comprises phenol, the aldehyde or the ketone comprises acetone, and the bisphenol comprises bisphenol A.

Embodiment 16

The catalyst of any one of the preceding embodiments, wherein the sulfonated, cross-linked polystyrene comprises 1 to 15 mol %, or 1 to 10 mol %, or 1 to 5 mol % of a repeat unit derived from a cross-linker relative to a total amount of repeat units.

In general, the disclosure can alternately comprise, consist of, or consist essentially of, any appropriate components herein disclosed. The disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The terms "a" and "an" do not denote a limitation of quantity, but rather denote the presence of at least one of the referenced item. The term "or" means "and/or" unless clearly indicated otherwise by context. Reference throughout the specification to "an embodiment", "another embodiment", "some embodiments", and so forth, means that a particular element (e.g., feature, structure, step, or characteristic) described in connection with the embodiment is included in at least one embodiment described herein, and may or may not be present in other embodiments. In addition, it is to be understood that the described elements may be combined in any suitable manner in the various embodiments. "Optional" or "optionally" means that the subsequently described event or circumstance may or may not occur, and that the description includes instances where the event occurs and instances where it does not. The term "combination" is inclusive of blends, mixtures, alloys, reaction products, and the like.

The endpoints of all ranges directed to the same component or property are inclusive of the endpoints, are independently combinable, and include all intermediate points. For example, ranges of "up to 25 wt %, or 5 to 20 wt %" is inclusive of the endpoints and all intermediate values of the ranges of "5 to 25 wt %," for example, 10 to 23 wt %, etc.

In general, the compositions, methods, and articles can alternatively comprise, consist of, or consist essentially of, any ingredients, steps, or components herein disclosed. The compositions, methods, and articles can additionally, or alternatively, be formulated, conducted, or manufactured so as to be devoid, or substantially free, of any ingredients, steps, or components not necessary to the achievement of the function or objectives of the present claims.

Unless defined otherwise, technical and scientific terms used herein have the same meaning as is commonly understood by one of skill in the art to which this disclosure belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A catalyst comprising:
    a porous carrier having 5 to 200 pores per 2.54 centimeters and a pore volume of at least 90 vol % based on the total volume of the porous carrier; wherein the porous carrier comprises one or both of carbon and a metal; and
    a sulfonated, cross-linked polystyrene located on at least part of a surface of the porous carrier.

2. The catalyst of claim 1, wherein the sulfonated, cross-linked polystyrene is grafted onto a thermoplastic layer located on the surface of the porous carrier.

3. A catalyst comprising,
    a porous carrier having 5 to 200 pores per 2.54 centimeters and a pore volume of at least 90 vol % based on the total volume of the porous carrier; wherein the porous carrier comprises one or both of carbon and a metal; and
    a sulfonated, cross-linked polystyrene located on at least part of a surface of the porous carrier; wherein the sulfonated, cross-linked polystyrene comprises 0.5 to 20 mol % of a repeat unit derived from a cross-linker relative to a total amount of repeat units.

4. The catalyst of claim 1, wherein the catalyst has an initial acid content of 0.01 to 0.2 milli-equivalents of acid groups per $cm^3$ of the catalyst.

5. The catalyst of claim 4, wherein, when introduced to a solution comprising phenol, acetone, or a combination thereof at a temperature of 75° C. for 24 hours, the sulfonated, cross-linked polystyrene retains at least 75 wt % of the initial acid content.

6. A method of making the catalyst of claim 1, comprising:
    polymerizing a polymerization mixture comprising a styrene monomer and a cross-linker in the presence of the porous carrier to form a polystyrene coated porous carrier having a cross-linked polystyrene located on the at least part of the surface of the porous carrier;
    separating the polystyrene coated porous carrier from the polymerization mixture;
    further polymerizing the cross-linked polystyrene after the separating; and
    sulfonating the further polymerized cross-linked polystyrene to form the catalyst.

7. The method of claim 6, further comprising coating the porous carrier with a thermoplastic layer prior to the polymerizing.

8. The method of claim 6, wherein the polymerization mixture comprises at least one thermal initiator.

9. A method of making a catalyst, comprising:
plasma treating, corona treating, or ozone treating a porous carrier to form a treated porous carrier; wherein the porous carrier has 5 to 200 pores per 2.54 centimeters and a pore volume of at least 90 vol % based on the total volume of the porous carrier; wherein the porous carrier comprises one or both of carbon and a metal;
polymerizing a polymerization mixture comprising a styrene monomer and a cross-linker in the presence of the treated porous carrier to form a polystyrene coated porous carrier having a cross-linked polystyrene located on the at least part of the surface of the treated porous carrier;
separating the polystyrene coated porous carrier from the polymerization mixture;
further polymerizing the cross-linked polystyrene after the separating; and
sulfonating the further polymerized cross-linked polystyrene to form the catalyst.

10. The method of claim 6, wherein the cross-linker is present in the polymerization mixture in an amount of 0.5 to 20 mol % based on the total moles of the cross-linker and the styrene monomer.

11. The method of claim 6, wherein the sulfonating comprises:
introducing a swelling agent to the further polymerized cross-linked polystyrene to form a swollen polystyrene;
introducing a sulfonating agent to the swollen polystyrene to form the sulfonated cross-linked polystyrene; and
washing the sulfonated cross-linked polystyrene.

12. The method of claim 6, wherein the method is performed in an inert environment and under a flow of an inert material.

13. A method for producing a bisphenol comprising:
reacting a phenolic compound with a reactant comprising one or both of an aldehyde and a ketone in the presence of the catalyst of claim 1 to produce the bisphenol.

14. The method of claim 13, wherein the phenolic compound comprises phenol, the aldehyde or the ketone comprises acetone, and the bisphenol comprises bisphenol A.

15. The catalyst of claim 3, wherein the sulfonated, cross-linked polystyrene comprises 1 to 15 mol % of a repeat unit derived from a cross-linker relative to a total amount of repeat units.

16. The method of claim 11, wherein the swelling agent comprises chloroform, 1,2 dichloroethane, or a combination thereof.

17. The method of claim 11, wherein the sulfonating agent comprises sulfur trioxide, sulfuric acid, or a combination thereof.

18. The method of claim 12, wherein the inert material consists essentially of nitrogen.

* * * * *